United States Patent
Srinivasan Natesan et al.

(10) Patent No.: US 10,339,824 B2
(45) Date of Patent: Jul. 2, 2019

(54) SYSTEM AND METHOD FOR EFFECTUATING DYNAMIC SELECTION AND PRESENTATION OF QUESTIONS DURING PRESENTATION OF RELATED CONTENT

(71) Applicant: KONINKLIJKE PHILIPS N.V., Eindhoven (NL)

(72) Inventors: Anand Srinivasan Srinivasan Natesan, Chennai (IN); Rithesh Sreenivasan, Bangalore (IN); Rajendra Singh Sisodia, Bhopal (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 247 days.

(21) Appl. No.: 15/357,079

(22) Filed: Nov. 21, 2016

(65) Prior Publication Data

US 2017/0178527 A1  Jun. 22, 2017

(51) Int. Cl.
| | |
|---|---|
| *G09B 7/00* | (2006.01) |
| *G16H 10/20* | (2018.01) |
| *G06K 9/00* | (2006.01) |
| *G09B 5/02* | (2006.01) |
| *G09B 7/04* | (2006.01) |
| *G09B 7/08* | (2006.01) |
| *G11B 27/031* | (2006.01) |
| *G06F 19/00* | (2018.01) |
| *G06F 16/70* | (2019.01) |

(52) U.S. Cl.
CPC .............. *G09B 7/00* (2013.01); *G06F 16/70* (2019.01); *G06F 19/34* (2013.01); *G06K 9/00718* (2013.01); *G09B 5/02* (2013.01); *G09B 7/04* (2013.01); *G09B 7/08* (2013.01); *G11B 27/031* (2013.01); *G16H 10/20* (2018.01)

(58) Field of Classification Search
CPC ........................................................ G09B 7/00
USPC .......................................................... 434/353
See application file for complete search history.

(56) References Cited

U.S. PATENT DOCUMENTS

| | | |
|---|---|---|
| 2003/0022141 A1 | 1/2003 | Packard |
| 2008/0032267 A1 | 2/2008 | Suzansky |
| 2008/0268413 A1 | 10/2008 | Leichner |
| 2011/0161107 A1 | 6/2011 | Goldberg et al. |

(Continued)

FOREIGN PATENT DOCUMENTS

| | | |
|---|---|---|
| WO | 2009023802 A1 | 2/2009 |
| WO | 2011016023 A1 | 2/2011 |
| WO | 2014066875 A1 | 5/2014 |

OTHER PUBLICATIONS

Georgios TH Papadopoulos et al: "Ontology-Driven Semantic Video Analysis Using Visual Information Objects", Dec. 5, 2007, Semantic Multimedia; Lecture Notes in Computer Science, Springer Berlin Heidelberg, Berlin Heidelberg, pp. 56-69, XP019084632, ISBN: 978-3-540-77033-6 The Whole Document.

*Primary Examiner* — Kesha Frisby (57) ABSTRACT

This disclosure describes a system that delivers content (e.g. multimedia video), and analyzes and aggregates feedback of a user viewing the content. The user may interact with the multimedia video in the form of answering questions which are dynamically placed between video segments. The system may determine the response type of the user for a given question. The system may handle both positive and negative responses (e.g. correct and incorrect responses to questions). The system may help the user navigate the segments of the video.

15 Claims, 3 Drawing Sheets

(56) References Cited

U.S. PATENT DOCUMENTS

2011/0172499 A1 7/2011 Simons-Nikolova et al.
2015/0026184 A1 1/2015 Ossikine

SYSTEM AND METHOD FOR EFFECTUATING DYNAMIC SELECTION AND PRESENTATION OF QUESTIONS DURING PRESENTATION OF RELATED CONTENT

CROSS-REFERENCE TO PRIOR APPLICATIONS

This application claims the benefit of or priority of foreign application IN6802/CHE/2015 filed Dec. 21, 2015, all of which are incorporated herein in whole by reference.

BACKGROUND

1. Field

The present disclosure pertains to a system and method for effectuating dynamic selection and presentation of questions during presentation of related content.

2. Description of the Related Art

Coaching a user during presentation of content to the user is an effective means in helping the user to understand a topic that needs to be understood by the user. Such coaching can relate to different and varying topics such as health care and education, and be used to facilitate e-learning. The content for coaching may be in the form of a video, text, audio and/or other forms.

SUMMARY

Accordingly, one or more aspects of the present disclosure relate to a system configured to effectuate dynamic selection and presentation of questions during presentation of related video content. The system comprises one or more hardware processors and/or other components. The one or more hardware processors are configured by machine-readable instructions to effectuate presentation of the content to a user, the content comprising one or both of information related to medical conditions experienced by the user or information related to an education course taken by the user, the content including one or more semantic concepts, an individual semantic concept indicated by a plurality of linked keywords corresponding to an individual topic of the content; evaluate the content to determine the one or more semantic concepts based on an evaluation parameter, the evaluation parameter including one or more of a type of the content, a complexity of the content, a link with other semantic concepts, or content segments; effectuate presentation of one or both of a query or a survey corresponding to the one or more semantic concepts to the user, the one or both of the query or the survey determined based on the content evaluation, such that a timing of the presentation of one or both of the query or the survey is determined by at least one user evaluation criteria, wherein the one or both of the query or the survey are selected and/or generated based on a semantic analysis of the content during the presentation of the content; evaluate interaction of the user with the content, the evaluation including determining whether the user answered one or both of the query or the survey correctly or incorrectly; and responsive to determining that the user answered correctly, effectuate presentation of additional content to the user, the additional content comprising one or both of new information related to the one or more semantic concepts or new information relating to other semantic concepts; or responsive to determining that the user answered incorrectly, effectuate presentation of a query or a survey corresponding to a simpler. semantic concept.

Another aspect of the present disclosure relates to a method for effectuating dynamic selection and presentation of questions during presentation of related video content with a system. The system comprises one or more hardware processors and/or other components. The method comprises effectuating presentation of the content to a user, the content comprising one or both of information related to medical conditions experienced by the user or information related to an education course taken by the user, the content including one or more semantic concepts, an individual semantic concept indicated by a plurality of linked keywords corresponding to an individual topic of the content; evaluating the video content to determine the one or more semantic concept based on an evaluation parameter, the evaluation parameter including one or more of a type of video content, a complexity of video content, a link with other semantic concepts, or content segments; effectuating presentation of one or both of a query or a survey corresponding to the one or more semantic concepts to the user, the one or both of the query or the survey determined based on the content evaluation, such that a timing of the presentation of one or both of the query or the survey is determined by at least one user evaluation criteria, wherein the one or both of the query or the survey are selected and/or generated based on a semantic analysis of the content during the presentation of the content; evaluating interaction of the user with the content, the evaluation including determining whether the user answered the one or both of the query or the survey correctly or incorrectly; and responsive to determining that the user answered correctly, effectuating presentation of additional content to the user, the additional content comprising one or both of new information related to the one or more semantic concepts or new information relating to other semantic concepts; or responsive to determining that the user answered incorrectly, effectuating presentation of a query or a survey corresponding to a simpler semantic concept.

Still another aspect of present disclosure relates to a system for effectuating dynamic selection and presentation of questions during presentation of related video content. The system comprises means for effectuating presentation of the content to a user, the content comprising one or both of information related to medical conditions experienced by the user or information related to an education course taken by the user, the content including one or more semantic concepts, an individual semantic concept indicated by a plurality of linked keywords corresponding to an individual topic of the content; means for evaluating the content to determine the one or more semantic concepts based on an evaluation parameter, the evaluation parameter including one or more of a type of the content, a complexity of the content, a link with other semantic concepts, or content segments; means for effectuating presentation of one or both of a query or a survey corresponding to the one or more semantic concepts to the user, one or both of the query or the survey determined based on the content evaluation, such that a timing of the presentation of one or both of the query or the survey is determined by at least one user evaluation criteria, wherein the one or both of the query or the survey are selected and/or generated based on a semantic analysis of the content during the presentation of the content; means for evaluating interaction of the user with the content, the evaluation including determining whether the user answered one or both of the query or the survey correctly or incorrectly; and responsive to determining that the user answered correctly, means for effectuating presentation of additional content to the user, the additional content comprising one or both of new information related to the one or more semantic concepts or new information relating to other semantic concepts; or responsive to determining that the user answered incorrectly, means for effectuating presentation of a query or a survey corresponding to a simpler semantic concept.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
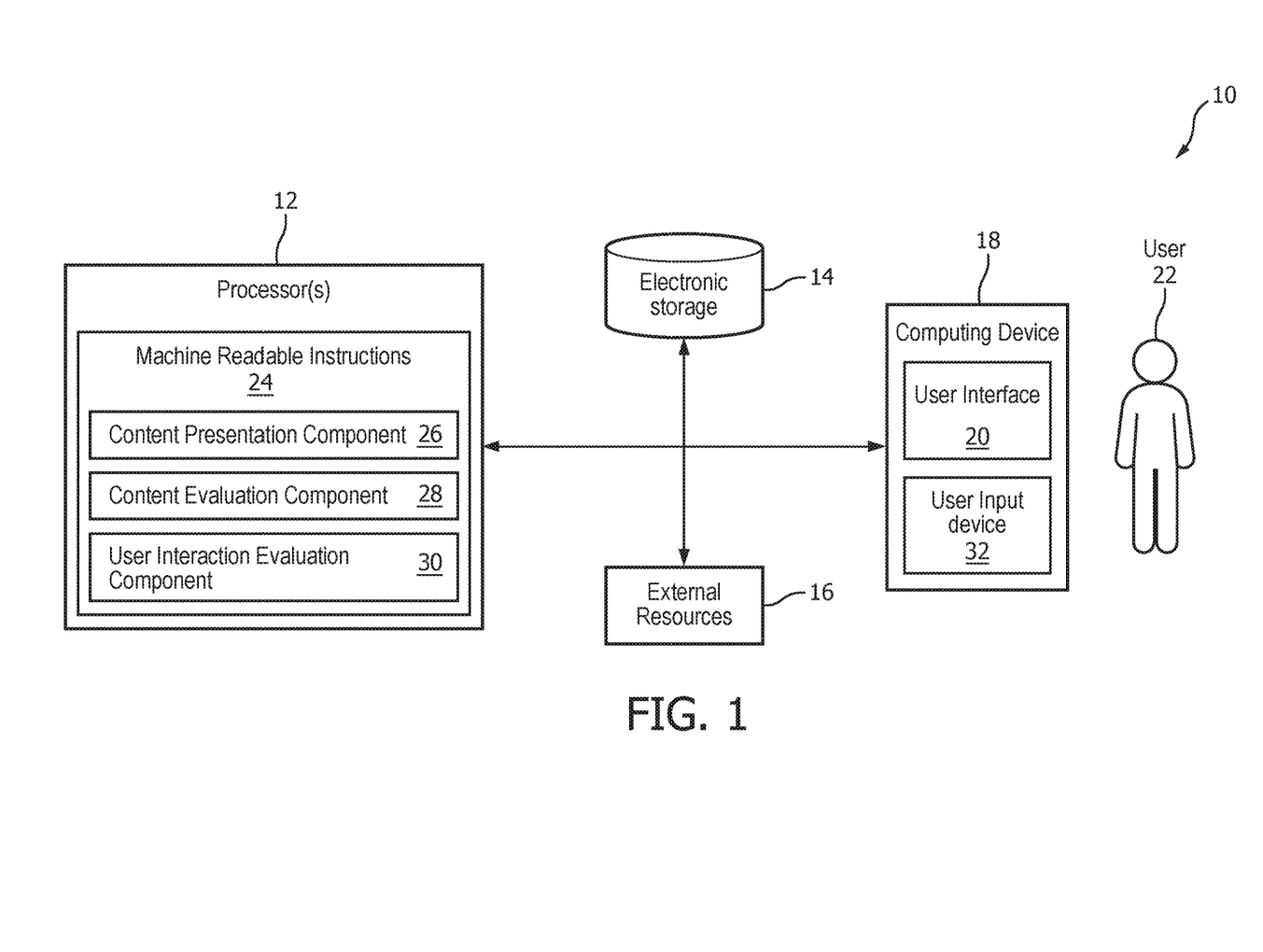
FIG. 1 is a schematic illustration of a system configured to effectuate dynamic selection and presentation of questions during presentation of related content.

FIG. 1 is a schematic illustration of a system 10 configured to effectuate dynamic selection and presentation of questions during presentation of related content. System 10 facilitates a better understanding of the concepts and topics in the delivered content. System 10 is configured to provide coaching to the user coordinated with delivery of the content, such that the delivered content may become more effective because of the inclusion of interactions between the user and the content facilitated by system 10. The interactions may be facilitated through a query and/or a survey, and/or responses corresponding to the query and/or the survey. The interactions may be timed for specific instants during the presentation of the content.

Present methods used to suggest various timings for the inclusion of an interaction during presentation of content rely on simple keyword identification of words in the content, resulting in the interactions being placed at a predetermined location and/or instance during the course of content presentation. This approach is not specific to a particular user. Moreover, this approach does not facilitate determining a depth and/or breadth of understanding of concepts discussed in the content by the user.

Present content delivery techniques were not designed with flexibility for content adjustment during the course of coaching through content delivery. Thus the extent to which the content can be altered and/or rearranged and/or modified with such techniques is limited. This approach is not tailored to a specific user, and results in a lack of effectiveness in meeting the goal for which the content is presented and/or the user is coached.

It is important to ensure that the user has understood the content and/or the information conveyed through the content at specific instances, before proceeding further so as to make the coaching meaningful and effective in meeting the goal and/or the purpose for which the user is exposed to such content.

System 10 is configured to deliver content (e.g. multimedia video and/or other content), and analyze and aggregate feedback of a user 22 viewing the content. User 22 interacts with the (for example) multimedia video in the form of answering questions which are dynamically placed between video segments. In some embodiments, system 10 is configured to determine the response type of user 22 for a given question. In some embodiments, system 10 is configured to respond to both positive and negative responses (e.g. correct and incorrect responses to questions). In some embodiments, system 10 is configured to help user 22 navigate segments of the video. For example a user is presented with content (video or text) about a particular concept (course taken at college or information about a medical condition). System 10 analyzes the content to create questions based on semantic concepts that are identified by keywords in the presented content and present the questions to the user. A timing for presenting the questions to the user is determined based on what needs to be evaluated (e.g. if user comprehension is to be tested, then the question is placed at the end of the content presentation. But if both comprehension and memorization are to be tested, then two questions at different intervals may be presented to the user). Responsive to the user providing a correct answer to the question, system 10, presents additional content. Responsive to the user providing an incorrect answer, system 10 presents a new question corresponding to a simpler semantic concept. If the user answers the question corresponding to the simpler concept, system 10 re-presents at least a portion of the previous content. In some embodiments, system 10 includes one or more of a processor 12, a computing device 18, electronic storage 14, external resources 16, and/or other components.

Processor 12 is configured to provide information processing capabilities in system 10. As such, processor 12 may comprise one or more of a digital processor, an analog processor, a digital circuit designed to process information, an analog circuit designed to process information, a state machine, and/or other mechanisms for electronically processing information. Although processor 12 is shown in FIG. 1 as a single entity, this is for illustrative purposes only. In some embodiments, processor 16 may comprise a plurality of processing units. These processing units may be physically located within the same device (e.g., a server), or processor 12 may represent processing functionality of a plurality of devices operating in coordination (e.g., a server, computing device 18 associated with user 22, devices that are part of external resources 16, and/or other devices.)

As shown in FIG. 1, processor 12 is configured via machine-readable instructions 24 to execute one or more computer program components. The one or more computer program components may comprise one or more of a content presentation component 26, a content evaluation component 28, a user interaction evaluation component 30, and/or other components. Processor 12 may be configured to execute components 26, 28, and/or 30 by software; hardware; firmware; some combination of software, hardware, and/or firmware; and/or other mechanisms for configuring processing capabilities on processor 12.

It should be appreciated that although components 26, 28, and 30 are illustrated in FIG. 1 as being co-located within a single processing unit, in embodiments in which processor 12 comprises multiple processing units, one or more of components 26, 28, and/or 30 may be located remotely from the other components. The description of the functionality provided by the different components 26, 28, and/or 30 described below is for illustrative purposes, and is not intended to be limiting, as any of components 26, 28, and/or 30 may provide more or less functionality than is described. For example, one or more of components 26, 28, and/or 30 may be eliminated, and some or all of its functionality may be provided by other components 26, 28, and/or 30. As another example, processor 12 may be configured to execute one or more additional components that may perform some or all of the functionality attributed below to one of components 26, 28, and/or 30.

Content presentation component 26 is configured to effectuate presentation of the content to user 22 and/or other users. The content is displayed on computing device 18 and/or other devices. Computing device 18 comprises a user interface 20 facilitating presentation of the content to user 22. Computing device 18 comprises a user input device 32 facilitating entering and/or selecting responses by user 22. In some embodiments, user input device 32 includes a mouse, a touchscreen, and/or other components (e.g., as described below related to computing device 18) facilitating selecting an answer choice in a multiple choice query or survey and a keyboard (and/or other components as described below) facilitating typing answers to a corresponding query or survey.

Content presentation component 26 is configured to effectuate presentation of content to user 22. In some embodiments, the content includes one or more of information related to medical conditions experienced by user 22, information related to an education course taken by user 22, information related to completion of a task assigned as a part of a care plan or program, and/or other content. In some embodiments, the content includes one or more semantic concepts. An individual semantic concept may be indicated by a plurality of linked keywords corresponding to an individual topic of the video content. For example, the at least one semantic concept may include semantic concepts such as Heart Attack, High Blood Pressure, Edema, Echo, and/or other semantic concepts. In some embodiments, multiple semantic concepts are included in the delivered content. For example, Blood pressure, nutrition, exercise, genetic heredity, and/or other semantic concepts may be presented to the user in one setting.

Content presentation component 26 is configured to effectuate presentation of one or more of a query, a survey, and/or other user interactions corresponding to the semantic concept to user 22. The query, the survey, and/or the other user interactions may ensure that user 22 has understood the content or of the information conveyed through the content, before proceeding further. In some embodiments, the one or more of the query, the survey, and/or other user interactions may be determined based on the content evaluation (described below).

A timing of the presentation of the one or more of the query, the survey, and/or other user interactions may be determined based on at least one user evaluation criteria. In some embodiments, user evaluation criteria includes one or more of the user 22's capability to memorize, recognize, recall, interpret, describe, or organize the content. In some embodiments, the one or more of the query, the survey, and/or other user interactions are selected and/or generated based on a semantic analysis of the content during the presentation of the video content. In some embodiments, the one or more of the query, the survey, and/or other user interactions may be presented after a delayed period. The delayed period is determined based on the user evaluation criteria. For example, if the user evaluation criteria is memorization and content is presented at a timestamp T, the one or more of the query, the survey, and/or other user interactions may be presented at timestamp T+X, where X represents content retention time of the user. Evaluating user 22 includes semantically analyzing keywords in a response provided by user 22 to the query, the survey, and/or other user interaction. For example, in a multimedia video, if heart failure and its symptoms are presented and a definition of "heart failure" is explained at 'T' second timestamp, content presentation component 26 may present a question regarding memorization of the presented content at 'T+X' second timestamp (delayed period), where X may be the concept retention time. If user 22 is unable to recall the concept at delayed period, user 22 may be evaluated, via user interaction evaluation component 30 (described below), as "weak" in memorization. Content presentation component 26 may present future queries, surveys, and/or other user interactions with shorter delayed period 'T+Y', where Y<X, until user 22's memorization skills improve and/or optimal time of user 22's retention capability is determined.

In some embodiments, content presentation component 26 is configured to, responsive to a determination by user interaction evaluation component 30 (described below), that user 22 answered the query, the survey, and/or other user interaction correctly (positive response), effectuate presentation of additional content to the user. In some embodiments the additional content may comprise one or more of new information related to the semantic concept, new information relating to other semantic concepts, and/or other additional content. In some embodiments, content presentation component 26 is configured such that effectuating presentation of the additional content includes one or more of fragmenting, reordering, altering, modifying, replacing, or combining portions of the additional content. Altering and/or modifying identified semantic concepts may include changing textual or visual information corresponding to the identified semantic concept prior to presentation. Fragmenting identified semantic concepts may include dividing the identified semantic concepts into smaller portions and presenting each of the smaller portions independent of one another. Combining identified semantic concepts may include combining a plurality of similar semantic concepts and/or a plurality of semantic concept segments prior to presentation. Replacing identified semantic concepts may include substituting one semantic concept for another semantic concept. For example, semantic concept of High Blood Pressure may be presented in fragmented components of nutrition, exercise, genetic heredity, and/or other components.

In some embodiments, content presentation component 26 is configured to, responsive to a determination by user interaction evaluation component 30 (described below), that user 22 answered the query, the survey, and/or other user interaction incorrectly, effectuate presentation of a query, a survey, and/or other user interaction corresponding to a simpler semantic concept. For example, a simpler semantic concept with respect to Diagnosis of Heart Failure may include Blood tests, Echo Cardiography, and/or other concepts. In this example, simpler semantic concepts are linked to a parent semantic concepts and are at a lower hierarchical level with respect to the parent semantic concept. For example, in a multimedia video, if heart failure and its symptoms are presented, content delivery component 26 may require user 22 to respond to the query, survey, and/or other user interaction based on a selected set of statements from the multimedia video which describe heart failure. Based on response provided by user 22, user 22's comprehension may be classified as strong or weak. Such determination may result in interventions such as presenting a simpler concept, with more illustration, dividing the concept into further sub concepts, and/or other interventions. Moreover, content delivery component 26 may present a new question that corresponds to a simpler semantic concept that may be more understandable. For example, a question based on the swelling of the legs (which is one individual symptom of heart failure) may be presented to user 22.

In some embodiments, content presentation component 26 is configured to, responsive to an incorrect response (negative response) provided by user 22 to the query, the survey, and/or other user interaction corresponding to the simpler semantic concept, effectuate presentation of simplified additional content. In some embodiments, the simplified additional content may comprise fragmented, reordered, altered, modified, replaced, or combined portions of the content for re-presentation to user 22. In some embodiments, content delivery component 26 may be configure to segment a multimedia video into smaller sub concepts, rearrange the segments based on semantic concept relations, and presents it to user 22. Content is segmented so that the user is presented with smaller and more comprehensible sub concepts before more difficult concepts are presented. Segmenting content also increases the flexibility of system 10 in presenting additional content and/or simplified additional content such that individual segments and/or a sequence of content segments are presented rather than the entirety of the content. For example, if user 22's understanding of heart failure is evaluated as poor, multimedia video corresponding to heart failure may be arranged in the following order of semantic concepts determined to be the easiest order to understand the semantic concepts: functioning of normal heart, heart related conditions (e.g. hypertension), heart failure symptoms, heart failure.

Figure 2:
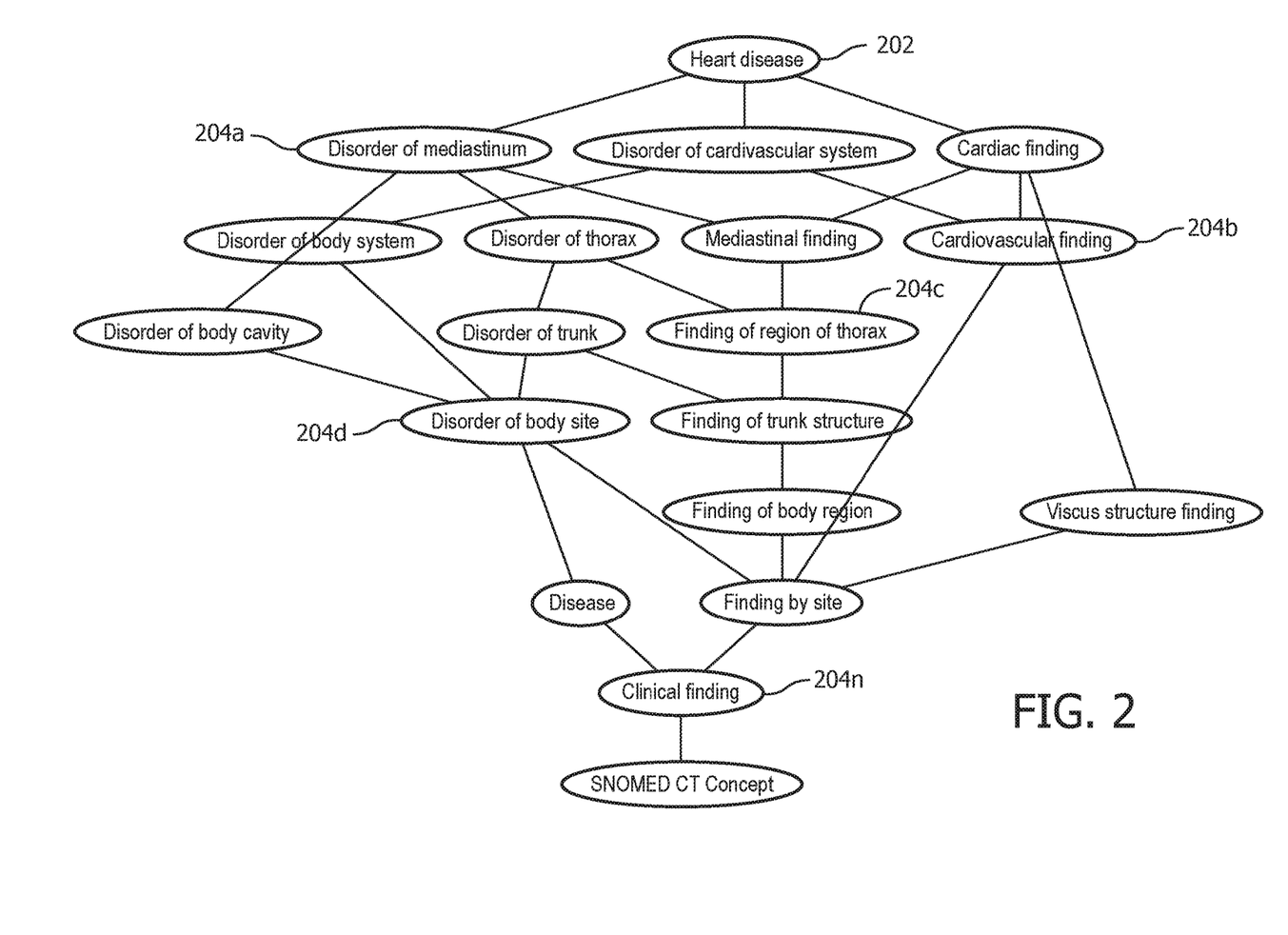
FIG. 2 illustrates depth and breadth of semantic concepts pertaining to heart disease according to one or more embodiments.

Content evaluation component 28 is configured to evaluate the content to determine the at least one semantic concept based on an evaluation parameter. The semantic concept are extracted based on text analysis of the content, by extracting the keywords related to a specific domain, and using a domain knowledge dictionary and ontology, the keywords are related with the semantic concept. In some embodiments the evaluation parameter may include one or more of a type of content, a complexity of content, a link with other semantic concepts, content segments, and/or other parameters. Content evaluation component is configured to determine the evaluation parameters based on an analysis of syntax of the content and/or other information. By way of a non-limiting example, FIG. 2 illustrates depth and breadth of a semantic concept 202 pertaining to a heart disease according to one or more embodiments. FIG. 2 illustrates various keywords 204a, 204b, 204c, 204d, . . . 204n associated with semantic concept 202. In some embodiments, content evaluation component 28 is configured to analyze the keywords linking various semantic concepts and various keywords within a given concept. For example, if the user can tell between difference between systolic blood pressure and diastolic blood pressure which are measurements related to high blood pressure semantic concept, the comprehension criteria with respect to high blood pressure is considered met. Moreover, based on user 22's comprehension of the high blood pressure semantic concept, user 22 understands how each of the blood pressure values impacts user 22's health, thus further educational material regarding controlling blood pressure would be readily understood by user 22. In some embodiments, content evaluation component 28 is configured to frame a question (e.g., for presentation to user 22 via content presentation component 26 and computing device 18) based on a depth and breadth of the semantic concept from the ontology in the content. For example, user 22 may be asked regarding the edema in the legs for a heart failure condition.

Returning to FIG. 1, user interaction evaluation component 30 is configured to evaluate interaction of user 22 with the content. In some embodiments, the evaluation may include determining whether the user answered one or more of the query, the survey, and/or other user interaction correctly or incorrectly. In some embodiments, user interaction evaluation component 30 is configured such that evaluating the interaction of user 22 with the content includes one or more of capturing, associating, arranging, or aggregating the query, the survey, and/or other user interaction and the response provided by the user. Interaction evaluation component 30 is configured to evaluate the interaction of user 22 with the content continuously during content presentation, periodically during content presentation, and/or at an end of and/or otherwise after the content presentation. In some embodiments, user interaction evaluation component 30 may be configured to, based on the evaluation criteria, links between content, and/or interaction of user 22 with the content, generate a summary report. The evaluation summary report comprises the evaluation of user interaction with respect to each of the evaluation criteria and each of the identified semantic concepts. For example, user 22 is evaluated with respect to an understanding of conditions of heart failure, symptoms, and precautions based on comprehension and memorization evaluation criteria and the results of each evaluation are recorded in the evaluation summary report. For example, if in a multimedia video, there are two instances of similar semantic concepts occurring within four minutes of one another, and interaction of user 22 with the content captured at times that correspond to the two semantic concepts reflects positive responses, the evaluation criteria of comprehension, re-interpretation and memorization may be considered as met with respect to the semantic concept. In some embodiments, user interaction evaluation component 30 may be configured to incentivize user 22 based on positive and/or negative responses provided by user 22. In some embodiments, user 22 may be incentivized in the form financial remuneration, which may motivate user 22 to use system 10 more effectively.

Electronic storage 14 comprises electronic storage media that electronically stores information. The electronic storage media of electronic storage 14 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 14 may be (in whole or in part) a separate component within system 10, or electronic storage 14 may be provided (in whole or in part) integrally with one or more other components of system 10 (e.g., computing device 18, processor 16, etc.). In some embodiments, electronic storage 14 may be located in a server together with processor 12, in a server that is part of external resources 16, in computing device 18 associated with user 22, and/or other users, and/or in other locations. Electronic storage 14 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 14 may store software algorithms, information determined by processor 12, information received via computing device 18 and/or other external computing systems, information received from external resources 16, and/or other information that enables system 10 to function as described herein. By way of a non-limiting example, electronic storage 14 may store a user profile for user 22 and/or other information.

External resources 16 include sources of information (e.g., databases, websites, etc.), external entities participating with system 10 (e.g., a medical records system of a health care provider that stores a health plan for user 22), one or more servers outside of system 10, a network (e.g., the internet), electronic storage, equipment related to Wi-Fi technology, equipment related to Bluetooth® technology, data entry devices, computing devices associated with individual users, and/or other resources. For example, in some embodiments, external resources 16 may include the database where the medical records including medical conditions, symptoms, and/or other information relating to user 22 are stored, and/or other sources of information. In some implementations, some or all of the functionality attributed herein to external resources 16 may be provided by resources included in system 10. External resources 16 may be configured to communicate with processor 12, computing device 18, electronic storage 14, and/or other components of system 10 via wired and/or wireless connections, via a network (e.g., a local area network and/or the internet), via cellular technology, via Wi-Fi technology, and/or via other resources.

Computing device 18 is configured to provide an interface between user 22, and/or other users and system 10. Computing device 18 is configured to provide information to and/or receive information from the user 22, and/or other users. For example, computing device 18 is configured to present a user interface 20 to user 22 to facilitate presentation of multimedia video to user 22. In some embodiments, user interface 20 includes a plurality of separate interfaces associated with computing device 18, processor(s) 12 and/or other components of system 10.

In some embodiments, computing device 18 is configured to provide user interface 20, processing capabilities, databases, and/or electronic storage to system 10. As such, computing device 18 may include processor(s) 12, electronic storage 14, external resources 16, and/or other components of system 10. In some embodiments, computing device 18 is connected to a network (e.g., the internet). In some embodiments, computing device 18 does not include processor(s) 12, electronic storage 14, external resources 16, and/or other components of system 10, but instead communicate with these components via the network. The connection to the network may be wireless or wired. For example, processor(s) 12 may be located in a remote server and may wirelessly cause display of user interface 20 to user 22 on computing device 18. In some embodiments, computing device 18 is a laptop, a personal computer, a smartphone, a tablet computer, and/or other computing devices. Examples of user input device 32 suitable for inclusion in computing device 18 include a touch screen, a keypad, touch sensitive and/or physical buttons, switches, a keyboard, knobs, levers, a display, speakers, a microphone, an indicator light, an audible alarm, a printer, and/or other interface devices. The present disclosure also contemplates that computing device 18 includes a removable storage interface. In this example, information may be loaded into computing device 18 from removable storage (e.g., a smart card, a flash drive, a removable disk) that enables the user 22, and/or other users to customize the implementation of computing device 18. Other exemplary input devices and techniques adapted for use with computing device 18 include, but are not limited to, an RS-232 port, RF link, an IR link, a modem (telephone, cable, etc.) and/or other devices.

Figure 3:
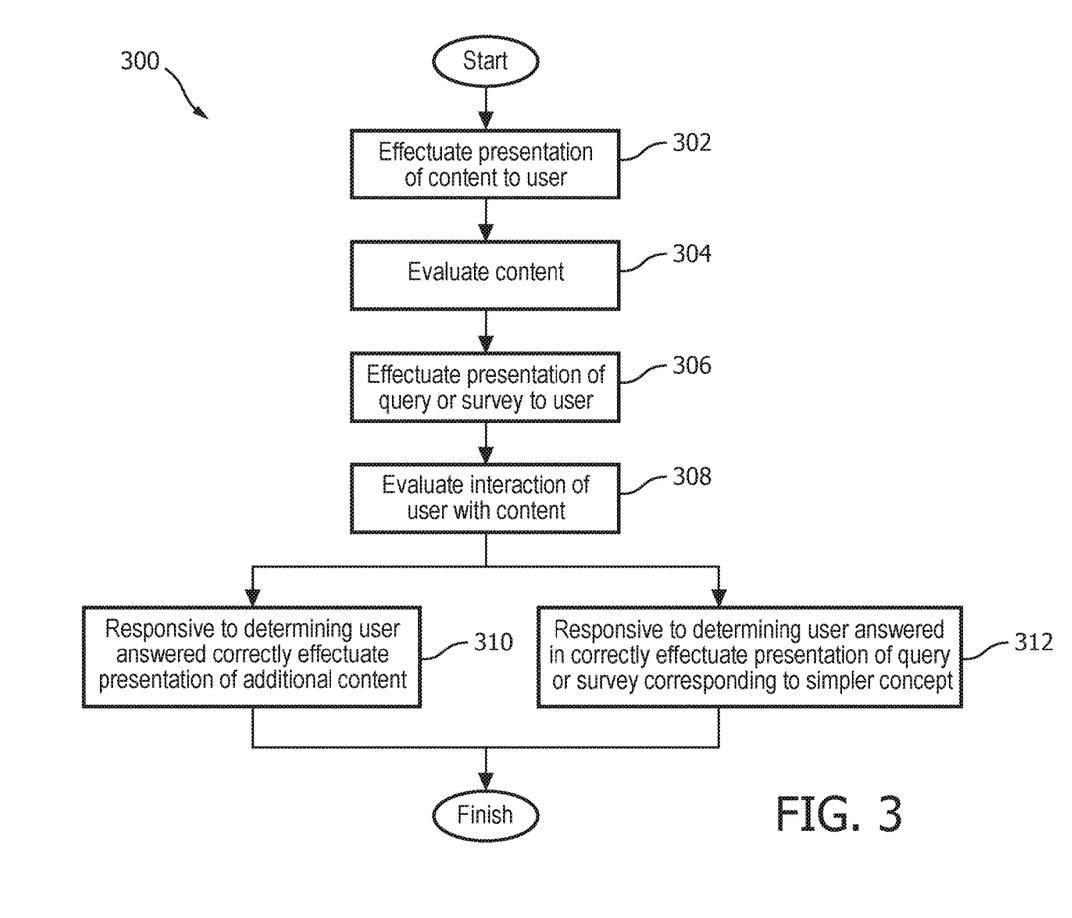
FIG. 3 illustrates a method for effectuating dynamic selection and presentation of questions during presentation of related content.

FIG. 3 illustrates a method 300 for delivering content, and analyzing and aggregating feedback of a user viewing the content with a system. The system comprises one or more hardware processors and/or other components. The one or more hardware processors are configured by machine readable instructions to execute computer program components. The computer program components comprise a content presentation component, a content evaluation component, a user interaction evaluation component, and/or other components. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, the content is presented to the user. In some embodiments, the content may include one or more of information related to medical conditions experienced by the user, information related to an education course taken by the user and/or other content. The content comprises one or more semantic concepts. An individual semantic concept may indicated by a plurality of linked keywords corresponding to an individual topic of the content. In some embodiments, operation 302 is performed by a processor component the same as or similar to content presentation component 26 (shown in FIG. 1 and described herein).

At an operation 304, the content is evaluated to determine the one or more semantic concepts based on an evaluation parameter. In some embodiments, the evaluation parameter includes one or more of a type of content, a complexity of content, a link with other semantic concepts, content segments, and/or other parameters. In some embodiments, operation 304 is performed by a processor component the same as or similar to content evaluation component 28 (shown in FIG. 1 and described herein).

At an operation 306, one or both of a query or a survey is presented to user. In some embodiments, one or both of query or survey are determined based on the content evaluation. In some embodiments, a timing of the presentation of one or more of the query, the survey, and/or other user interactions is determined by at least one user evaluation criteria. In some embodiments, the user evaluation criteria includes one or more of the user's capability to memorize, recognize, recall, interpret, describe, or organize the video content. In some embodiments, the one or more of the query, the survey, and/or other user interactions are selected and/or generated based on a semantic analysis of the video content during the presentation of the video content In some embodiments, operation 306 is performed by a processor component the same as or similar to content presentation component 26 (shown in FIG. 1 and described herein).

At an operation 308, an interaction of user with content is evaluated. In some embodiments, evaluating interaction of the user with the content includes semantically analyzing keywords in a response provided by the user to the one or more of the query, the survey, and/or other user interactions. In some embodiments, the evaluation includes determining whether the user answered the one or more of the query, the survey, and/or other user interactions correctly or incorrectly. In some embodiments, evaluating the interaction of user with content includes one or more of capturing, associating, arranging, or aggregating the query or the survey and the response provided by the user corresponding to the content continuously, periodically, or at an end of the content. In some embodiments, operation 308 is performed by a processor component the same as or similar to user interaction evaluation component 30 (shown in FIG. 1 and described herein).

At an operation 310, responsive to determining that the user answered correctly, additional content is presented to user. In some embodiments, the additional content comprises one or more of new information related to the one or more semantic concepts, new information relating to other semantic concepts, and/or other additional content. In some embodiments, presenting additional content includes one or more of fragmenting, reordering, altering, modifying, replacing, and/or combining portions of the additional content. In some embodiments, operation 310 is performed by a processor component the same as or similar to content presentation component 26 (shown in FIG. 1 and described herein).

At operation 312, responsive to determining that the user answered incorrectly, one or more of a query, a survey, and/or other user interactions corresponding to a simpler semantic concept is presented to user. In some embodiments, responsive to an incorrect response provided by the user to the one or more of the query, the survey, and/or other user interactions corresponding to the simpler semantic concept, simplified additional content is re-presented to user. In some embodiments, the simplified additional content comprises fragmented, reordered, altered, modified, replaced, or combined portions of the content. In some embodiments, operation 312 is performed by a processor component the same as or similar to content presentation component 26 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to effectuate dynamic selection and presentation of questions during presentation of related video content, the system comprising one or more hardware processors configured by machine-readable instructions to:

effectuate, on a computing device, presentation of the video content to a user, the video content comprising one or both of information related to medical conditions experienced by the user or information related to an education course taken by the user, the video content including one or more semantic concepts, an individual semantic concept indicated by a plurality of linked keywords corresponding to an individual topic of the video content;

evaluate, on the computing device, the video content to determine the one or more semantic concepts based on an evaluation parameter, the evaluation parameter including one or more of a type of the video content, a complexity of the video content, a link with other semantic concepts, or video content segments;

effectuate, on the computing device, presentation of one or both of a query or a survey corresponding to the one or more semantic concepts to the user, the one or both of the query or the survey determined based on the video content evaluation, such that a timing of the presentation of one or both of the query or the survey is determined by user evaluation criteria, wherein the one or both of the query or the survey are selected and/or generated based on a semantic analysis of the video content during the presentation of the video content;

evaluate, on the computing device, interaction of the user with the video content, the evaluation including determining whether the user answered one or both of the query or the survey correctly or incorrectly; and responsive to determining that the user answered correctly, effectuate presentation of additional video content to the user, the additional video content comprising one or both of new information related to the one or more semantic concepts or new information relating to other semantic concepts; or responsive to determining that the user answered incorrectly, effectuate presentation of a query or a survey corresponding to a simpler semantic concept.

2. The system of claim 1, wherein the one or more hardware processors are configured such that effectuating presentation of the additional video content includes one or more of fragmenting, reordering, altering, modifying, replacing, or combining portions of the additional video content.

3. The system of claim 1, wherein the one or more hardware processors are configured such that the user evaluation criteria include one or more of the user's capability to memorize, recognize, recall, interpret, describe, or organize the video content and evaluating interaction of the user with the video content includes semantically analyzing keywords in a response provided by the user to the query or the survey.

4. The system of claim 1, wherein the one or more hardware processors are further configured by machine-readable instructions to, responsive to an incorrect response provided by the user to the query or the survey corresponding to the simpler semantic concept, effectuate presentation of simplified additional video content, the simplified additional video content comprising fragmented, reordered, altered, modified, replaced, or combined portions of the video content for re-presentation to the user.

5. The system of claim 1, wherein the one or more hardware processors are configured such that evaluating the interaction of the user with the video content includes one or more of capturing, associating, arranging, or aggregating the query or the survey and the response provided by the user corresponding to the video content continuously, periodically, or at an end of the video content.

6. A method for effectuating dynamic selection and presentation of questions during presentation of related video content with a system including one or more hardware processors configured by machine-readable instructions, the method comprising:

effectuating, on a computing device, presentation of the video content to a user, the video content comprising one or both of information related to medical conditions experienced by the user or information related to an education course taken by the user, the video content including one or more semantic concepts, an individual semantic concept indicated by a plurality of linked keywords corresponding to an individual topic of the video content;

evaluating, on the computing device, the video content to determine the one or more semantic concept based on an evaluation parameter, the evaluation parameter including one or more of a type of video content, a complexity of video content, a link with other semantic concepts, or video content segments;

effectuating, on the computing device, presentation of one or both of a query or a survey corresponding to the one or more semantic concepts to the user, the one or both of the query or the survey determined based on the video content evaluation, such that a timing of the presentation of one or both of the query or the survey is determined by user evaluation criteria, wherein the one or both of the query or the survey are selected and/or generated based on a semantic analysis of the video content during the presentation of the video content;

evaluating, on the computing device, interaction of the user with the video content, the evaluation including determining whether the user answered the one or both of the query or the survey correctly or incorrectly; and responsive to determining that the user answered correctly, effectuating presentation of additional video content to the user, the additional video content comprising one or both of new information related to the one or more semantic concepts or new information relating to other semantic concepts; or responsive to determining that the user answered incorrectly, effectuating presentation of a query or a survey corresponding to a simpler semantic concept.

7. The method of claim 6, wherein effectuating presentation of the additional video content includes:

one or more of fragmenting, reordering, altering, modifying, replacing, or combining portions of the additional video content.

8. The method of claim 6, wherein the user evaluation criteria include one or more of the user's capability to memorize, recognize, recall, interpret, describe, or organize the video content and evaluating interaction of the user with the video content includes semantically analyzing keywords in a response provided by the user to the query or the survey.

9. The method of claim 6, further comprising, responsive to an incorrect response provided by the user to the query or the survey corresponding to the simpler semantic concept:

effectuating presentation of simplified additional video content, the simplified additional video content comprising fragmented, reordered, altered, modified, replaced, or combined portions of the video content for re-presentation to the user.

10. The method of claim 6, wherein evaluating the interaction of the user with the video content includes:

one or more of capturing, associating, arranging, or aggregating the query or the survey and the response provided by the user corresponding to the video content continuously, periodically, or at an end of the video content.

11. A system for effectuating dynamic selection and presentation of questions during presentation of related video content, the system comprising: means for effectuating presentation of the video content to a user, the video content comprising one or both of information related to medical conditions experienced by the user or information related to an education course taken by the user, the video content including one or more semantic concepts, an individual semantic concept indicated by a plurality of linked keywords corresponding to an individual topic of the video content;

means for evaluating, on a computing device, the video content to determine the one or more semantic concepts based on an evaluation parameter, the evaluation parameter including one or more of a type of the video content, a complexity of the video content, a link with other semantic concepts, or video content segments;

means for effectuating, on the computing device, presentation of one or both of a query or a survey corresponding to the one or more semantic concepts to the user, one or both of the query or the survey determined based on the video content evaluation, such that a timing of the presentation of one or both of the query or the survey is determined by user evaluation criteria, wherein the one or both of the query or the survey are selected and/or generated based on a semantic analysis of the video content during the presentation of the video content;

means for evaluating, on the computing device, interaction of the user with the video content, the evaluation including determining whether the user answered one or both of the query or the survey correctly or incorrectly; and responsive to determining that the user answered correctly, means for effectuating presentation of additional video content to the user, the additional video content comprising one or both of new information related to the one or more semantic concepts or new information relating to other semantic concepts;

or responsive to determining that the user answered incorrectly, means for effectuating presentation of a query or a survey corresponding to a simpler semantic concept.

12. The system of claim 11, wherein the means for effectuating presentation of the additional video content includes one or more of means for fragmenting, reordering, altering, modifying, replacing, or combining portions of the additional video content.

13. The system of claim 11, wherein the user evaluation criteria include one or more of the user's capability to memorize, recognize, recall, interpret, describe, or organize the video content and evaluating interaction of the user with the video content includes semantically analyzing keywords in a response provided by the user to the query or the survey.

14. The system of claim 11, further comprising, responsive to an incorrect response provided by the user to the query or the survey corresponding to the simpler semantic concept:

means for effectuating presentation of simplified additional video content, the simplified additional video content comprising fragmented, reordered, altered, modified, replaced, or combined portions of the video content for re-presentation to the user.

15. The system of claim 11, wherein the means for evaluating the interaction of the user with the video content includes one or more of means for capturing, associating, arranging, or aggregating the query or the survey and the response provided by the user corresponding to the video content continuously, periodically, or at an end of the video content.

* * * * *